(12) United States Patent
Reicher et al.

(10) Patent No.: US 11,900,265 B2
(45) Date of Patent: Feb. 13, 2024

(54) DATABASE SYSTEMS AND INTERACTIVE USER INTERFACES FOR DYNAMIC CONVERSATIONAL INTERACTIONS

(71) Applicant: MERATIVE US L.P., Ann Arbor, MI (US)

(72) Inventors: Murray A. Reicher, Rancho Santa Fe, CA (US); Stewart Nickolas, Austin, TX (US); David Boloker, Brookline, MA (US)

(73) Assignee: MERATIVE US L.P., Ann Arbor, MI (US)

( * ) Notice: Subject to any disclaimer, the term of this patent is extended or adjusted under 35 U.S.C. 154(b) by 1233 days.

(21) Appl. No.: 15/811,526

(22) Filed: Nov. 13, 2017

(65) Prior Publication Data

US 2019/0147346 A1 May 16, 2019

(51) Int. Cl.
| | | |
|---|---|---|
| *G06N 5/02* | (2023.01) | |
| *G16H 70/20* | (2018.01) | |
| *G16H 30/20* | (2018.01) | |
| *G06F 9/451* | (2018.01) | |
| *G06N 20/00* | (2019.01) | |
| *G06F 16/25* | (2019.01) | |
| *G06F 16/242* | (2019.01) | |
| *G06F 16/435* | (2019.01) | |

(52) U.S. Cl.
CPC .............. *G06N 5/02* (2013.01); *G06F 9/453* (2018.02); *G06F 16/243* (2019.01); *G06F 16/25* (2019.01); *G06F 16/437* (2019.01); *G06N 20/00* (2019.01); *G16H 30/20* (2018.01); *G16H 70/20* (2018.01)

(58) Field of Classification Search
CPC ........ G06N 5/00–048; G06N 20/00–20; G06F 16/25–258; G06F 16/242–2448; G16H 50/20
USPC ......................................... 706/45–61; 700/49
See application file for complete search history.

(56) References Cited

U.S. PATENT DOCUMENTS

| | | | |
|---|---|---|---|
| 9,690,861 B2 | 6/2017 | Boloor et al. | |
| 2002/0065684 A1* | 5/2002 | Schwalb | G16H 30/40 |
| | | | 128/920 |
| 2002/0133355 A1* | 9/2002 | Ross | G10L 15/1822 |
| | | | 704/275 |
| 2013/0184582 A1* | 7/2013 | Kanayama | A61B 8/463 |
| | | | 600/440 |

(Continued)

FOREIGN PATENT DOCUMENTS

WO WO 2017/070255 4/2017

OTHER PUBLICATIONS

David McSherry, 2011, "Conversational case-based reasoning in medical decision making", Artificial Intelligence in Medicine.*

(Continued)

*Primary Examiner* — Jue Louie
(74) *Attorney, Agent, or Firm* — Michael Best & Friedrich, LLP

(57) ABSTRACT

A conversation management system provides a conversational computing interface that manages verbal exchanges between a computer (e.g., artificial intelligence) and a human operator. In a medical embodiment, conversational input from the computing system is generated based on medical knowledge, uses deep learning algorithms, and/or intelligently tracks the state of a conversation so as to the most relevant data to the user.

17 Claims, 5 Drawing Sheets

(56) References Cited

U.S. PATENT DOCUMENTS

| | | | | |
|---|---|---|---|---|
| 2014/0074454 | A1* | 3/2014 | Brown | G10L 15/08 704/9 |
| 2014/0317080 | A1 | 10/2014 | Piraino et al. | |
| 2015/0023579 | A1* | 1/2015 | Fujimoto | G16H 15/00 382/132 |
| 2015/0066539 | A1 | 3/2015 | Sheffer et al. | |
| 2016/0147971 | A1* | 5/2016 | Kolowitz | G06F 3/0481 715/753 |
| 2016/0239564 | A1* | 8/2016 | Sohma | G06F 16/358 |
| 2017/0039322 | A1* | 2/2017 | Reicher | G06F 16/583 |
| 2017/0086790 | A1* | 3/2017 | Halmann | A61B 8/0858 |
| 2017/0228367 | A1* | 8/2017 | Pasupalak | G06F 16/90332 |
| 2017/0231592 | A1* | 8/2017 | Sevenster | G16H 30/40 600/407 |
| 2017/0243348 | A1* | 8/2017 | Sakamoto | G16H 15/00 |
| 2018/0174055 | A1* | 6/2018 | Tirumale | G06Q 10/10 |
| 2018/0365025 | A1* | 12/2018 | Almecija | G06F 3/04847 |
| 2019/0266495 | A1 | 8/2019 | Reicher et al. | |
| 2020/0265946 | A1* | 8/2020 | Benjamin | G16H 30/20 |

OTHER PUBLICATIONS

Robert Neßelrath, 2015, "SiAM-dp: An open development platform for massively multimodal dialogue systems in cyber-physical environments", PH.D. thesis, Universität des Saarlandes.*

Prange et al., Aug. 15-17, 2017, "A Multimodal Dialogue System for Medical Decision Support in Virtual Reality" Proceedings of the SIGDIAL 2017 Conference.*

Sonntag et al. "Prototyping Semantic Dialogue Systems for Radiologists", 2010, 2010 Sixth International Conference on Intelligent Environments.*

Sonntag et al. "Design and Implementation of a Semantic Dialogue System for Radiologists", Jan. 2017, arXiv:1701.07381.*

Sonntag, Nesserlrath, et al. "Supporting A Rapid Dialogue Engineering Process", 2009, Conference: Proceedings of the First International Workshop On Spoken Dialogue Systems Technology (IWSDS).*

Gudivada et al., "Content based image retrieval systems." Computer 28.9 (1995): 18-22.

Gudivada et al., "A unified approach to data modeling and retrieval for a class of image database applications." Multimedia database systems. Springer Berlin Heidelberg, 1996. 37-78.

Li et al., "Hierarchical image modeling for object-based media retrieval." Data & Knowledge Engineering 27.2 (1998): 139-176.

United States Patent Office Action for U.S. Appl. No. 16/409,473 dated Dec. 9, 2021 (8 pages).

Hung et al., "Towards a Context-Based Dialog Management Layer for Expert Systems," International Conference on Information, Process, and Knowledge Management, 2009, pp. 60-65.

United States Patent Office Action for U.S. Appl. No. 16/409,473 dated Mar. 31, 2022 (9 pages).

United States Patent Office Action for U.S. Appl. No. 16/409,473 dated Jul. 27, 2022 (15 pages).

United States Patent Office Action for U.S. Appl. No. 16/409,473 dated Feb. 13, 2023 (29 pages).

* cited by examiner

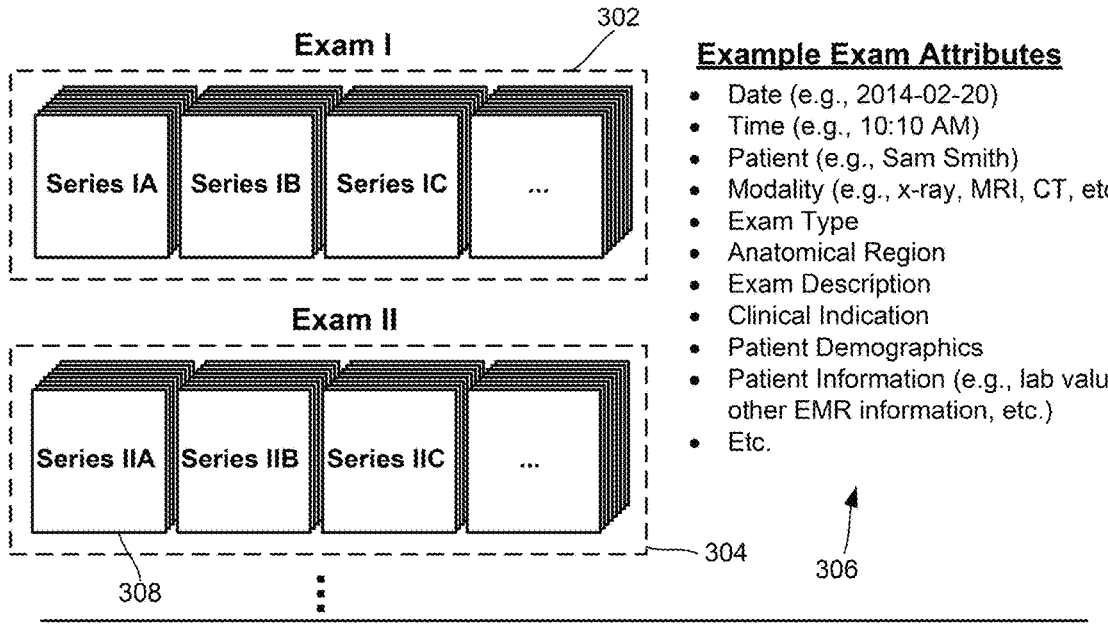

Example Exam Attributes
- Date (e.g., 2014-02-20)
- Time (e.g., 10:10 AM)
- Patient (e.g., Sam Smith)
- Modality (e.g., x-ray, MRI, CT, etc.)
- Exam Type
- Anatomical Region
- Exam Description
- Clinical Indication
- Patient Demographics
- Patient Information (e.g., lab values, other EMR information, etc.)
- Etc.

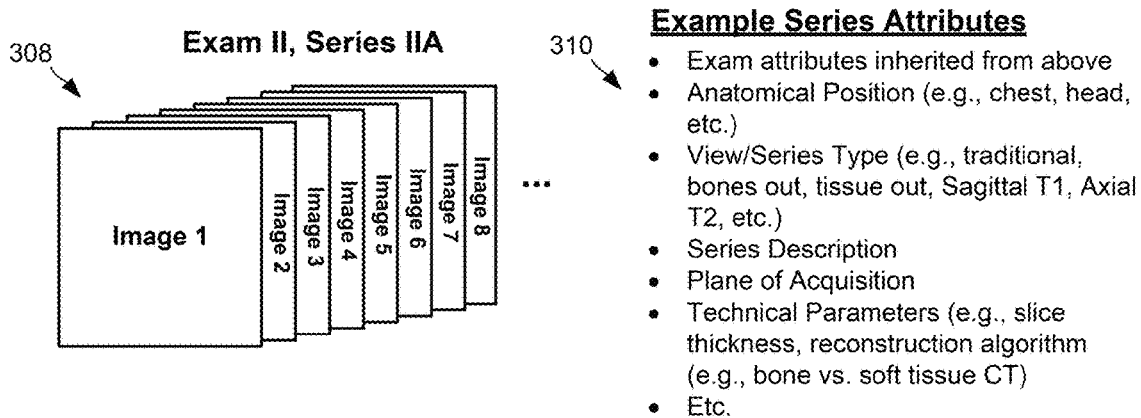

Example Series Attributes
- Exam attributes inherited from above
- Anatomical Position (e.g., chest, head, etc.)
- View/Series Type (e.g., traditional, bones out, tissue out, Sagittal T1, Axial T2, etc.)
- Series Description
- Plane of Acquisition
- Technical Parameters (e.g., slice thickness, reconstruction algorithm (e.g., bone vs. soft tissue CT)
- Etc.

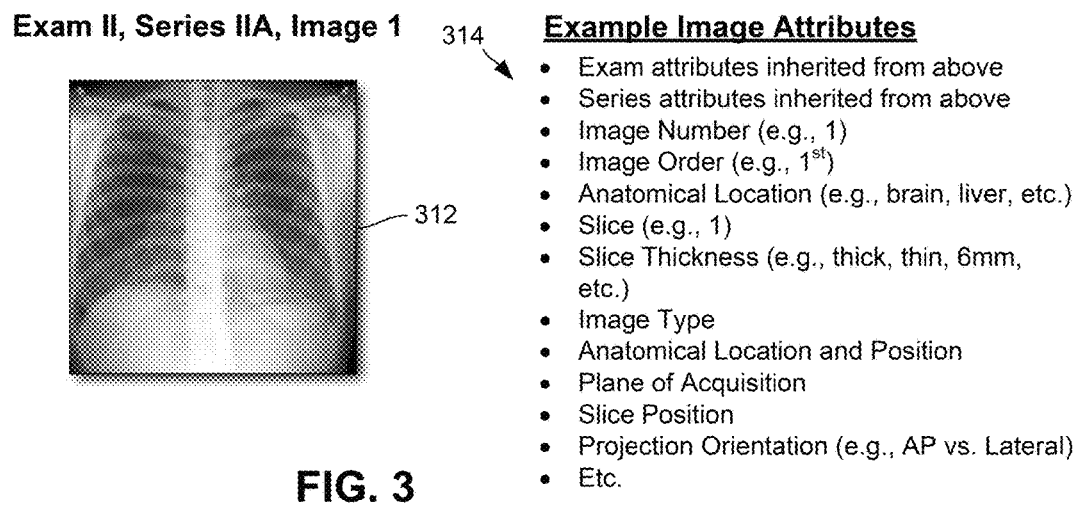

Example Image Attributes
- Exam attributes inherited from above
- Series attributes inherited from above
- Image Number (e.g., 1)
- Image Order (e.g., 1st)
- Anatomical Location (e.g., brain, liver, etc.)
- Slice (e.g., 1)
- Slice Thickness (e.g., thick, thin, 6mm, etc.)
- Image Type
- Anatomical Location and Position
- Plane of Acquisition
- Slice Position
- Projection Orientation (e.g., AP vs. Lateral)
- Etc.

FIG. 3

DATABASE SYSTEMS AND INTERACTIVE USER INTERFACES FOR DYNAMIC CONVERSATIONAL INTERACTIONS

TECHNICAL FIELD

Embodiments of the present disclosure relate to systems and techniques for accessing one or more databases and providing user interfaces for dynamic interactions with digital medical image data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Physicians and other healthcare workers that must view medical images face the challenge of dividing cognitive and visual attention between multiple tasks, such as viewing images, viewing patient histories, and creating reports. Simply stated, when a radiologist views a patient's medical imaging exam, he or she must often shift attention to view a prior report, current report, electronic health record, scanned document, or other source of information. Rather than thus dividing visual attention, a reading physician may instead receive audio input from a computer system that is relevant to the task at hand. Beginning in the early 1990's, picture archive and communication systems (PACS) began to offer multi-media capabilities, so that, for example, a physician could view the medical images of a current and prior exam while the system played an audio file of the conclusion of the prior exam's report.

SUMMARY

Disclosed herein are systems and methods for implementing conversational computing, including verbal exchanges between a computer (e.g., artificial intelligence) and a human operator. In a medical embodiment, conversational input from the computing system is generated based on medical knowledge, uses deep learning algorithms, and/or intelligently tracks the state of a conversation so as to provide the most relevant information to the user.

In one embodiment, the system and methods discussed herein combine a computerized image management system, a medical knowledge decision engine (with artificial intelligence), one or more data sources, and a conversational human interface to provide reading physicians context-sensitive audio (or audiovisual) that facilitates diagnostic processes. As a result of the conversational interface and these other technologies, the system minimizes cognitive distraction of the reading physician while providing cognitive assistance yielding a better diagnostic outcome.

The systems, methods, and devices described herein each have several aspects, no single one of which is solely responsible for its desirable attributes. Without limiting the scope of this disclosure, several non-limiting features will now be described briefly.

Disclosed herein are systems that, according to various embodiments, advantageously provide highly efficient, intuitive, and rapid dynamic interaction with medical images (including two-dimensional images and images rendered from three-dimensional image data) to enable users to participate in a "conversation" with a medical computing system related to medical data of interest to the user. The systems may include interactive user interfaces that are dynamically updated to provide information to the user and/or receive further inputs from the user.

Further, as described herein, the system may be configured and/or designed to generate user interface data useable for rendering the various interactive user interfaces described. The interactive user interfaces may be displayed on, for example, electronic displays (including, for example, touch-enabled displays) and/or used to establish conversations with practitioners.

It has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The present disclosure describes various embodiments of interactive and dynamic user interfaces that are the result of significant development. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interface via the inputs described herein may provide an optimized display of, and interaction with, image data (including medical images) and may enable a user to more quickly and accurately access, navigate, assess, and digest the image data than previous systems.

Various embodiments of the present disclosure provide improvements to various technologies and technological fields. For example, as described above, existing medical image interaction technology (including, e.g., Picture Archiving and Communication Systems, Electronic Medical Record Systems, and/or the like) is limited in various ways (e.g., image review may be cumbersome, comparison of images may be inefficient, etc.), and various embodiments of the disclosure provide significant improvements over such technology, such as by providing conversational computing capability to users. Additionally, various embodiments of the present disclosure are inextricably tied to computer technology. In particular, various embodiments rely on detection of user inputs via audio sensors, determination of words or phrases uttered by the user in the audio input, determining context of online medial image viewing activity of the user, tracking state of a conversation with the user, accessing a knowledge base to determine a next communication to provide to the user, and so on. Further, the implementation of the various embodiments of the present disclosure via computer technology enables many of the advantages described herein, including more efficient interaction with, and presentation of, various types of electronic image data.

In various embodiments, computer systems are disclosed that comprise one or more hardware computer processors in communication with one or more non-transitory computer readable storage devices, wherein the one or more hardware computer processors are configured to execute the plurality of computer executable instructions in order to cause the computer system to operations comprising one or more aspects of the above-described embodiments (including one or more aspects of the appended claims).

In various embodiments, computer-implemented methods are disclosed in which, under control of one or more hardware computing devices configured with specific computer executable instructions, one or more aspects of the above-described embodiments (including one or more aspects of the appended claims) are implemented and/or performed.

In various embodiments, computer readable storage mediums storing software instructions are disclosed, wherein, in response to execution by a computing system having one or more hardware processors, the software instructions configure the computing system to perform operations comprising one or more aspects of the above-described embodiments (including one or more aspects of the appended claims).

BRIEF DESCRIPTION OF THE DRAWINGS

The following drawings and the associated descriptions are provided to illustrate embodiments of the present disclosure and do not limit the scope of the claims. Aspects and many of the attendant advantages of this disclosure will become more readily appreciated as the same become better understood by reference to the following detailed description, when taken in conjunction with the accompanying drawings, wherein:

FIG. 3 is a diagram illustrating a display device of the system having images from four image series concurrently displayed in image panes displayed on the display device, such as may be automatically selected based on an spoken command from the user, according to an embodiment of the present disclosure.

DETAILED DESCRIPTION

Figure 1:
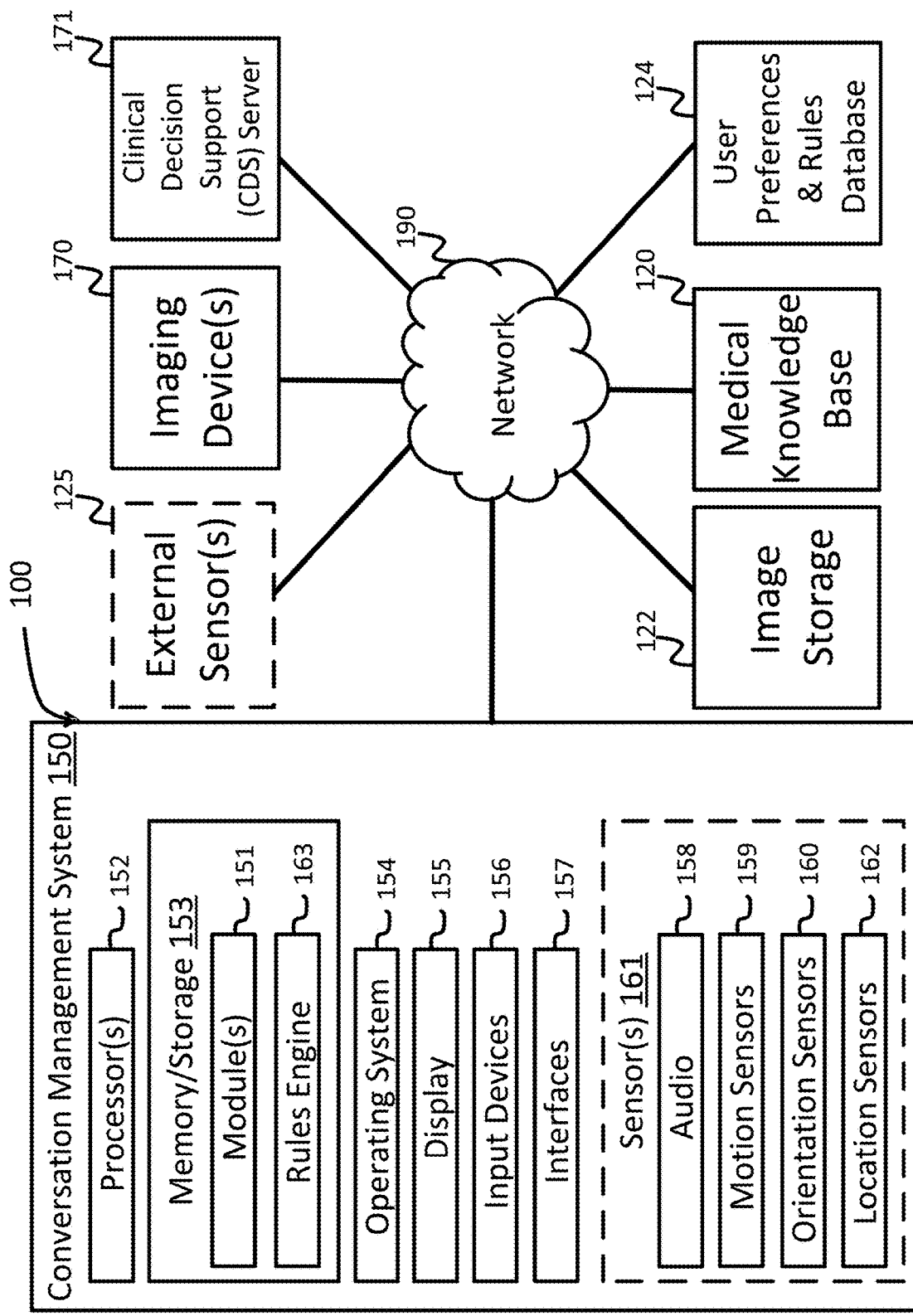
FIG. 1 is a block diagram showing various aspects of a computing system and network environment in which the computing system may be implemented, according to various embodiments of the present disclosure.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

I. Overview

As mentioned above, according to various embodiments systems are disclosed that combine a computerized image management system, a medical knowledge decision engine (with artificial intelligence), one or more data sources, and a conversational human interface to provide reading physicians context-sensitive audio (or audiovisual) that facilitates diagnostic processes. As a result of the conversational interface and these other technologies, the system minimizes cognitive distraction of the reading physician while providing cognitive assistance yielding a better diagnostic outcome.

As also mentioned above, according to various embodiments a data navigation system is disclosed in which a user may interact with medical images (including two-dimensional images and images rendered from three-dimensional image data) to enable detection of differences between related medical images and evaluation of medical images, such as by having a conversation with the computing system and/or interacting with interactive user interfaces.

In various embodiments described herein, images from one or more series and/or exams are automatically analyzed and sorted. In an embodiment, reference image data is alternatively, or also, sorted with images. The system enables fast and efficient evaluation and comparison of related images as a result of the sorting. For example, sorted images may be rapidly paged through to enable detailed comparison of images and detection of changes (including, e.g., changes in a medical condition of a patient). User interfaces of the system are thus dynamically updated to provide rapid comparison of images. Further, images from multiple series and/or exams, and/or images from other sources, may be automatically sorted by the system according to attributes associated with the images and rules and/or preferences of the user.

In an embodiment, the user (or the system automatically) may select an image from a series of a first exam, and the system automatically determines and displays one or more comparison images from other image series and/or exams. Images selected for comparison, and/or images that are sorted, may additionally be automatically registered and/or matched to enable more efficient comparison and evaluation by the user. Accordingly, a user may use the systems described herein to more quickly, thoroughly, and efficiently interact with medical images, as compared to previous systems.

In various embodiments, systems and methods are disclosed for matching related medical images and/or medical image series from multiple exams, automatically displaying medical images in particular arrangements, and automatically sorting medical images from related exams. In one example, a user selects a medical image, and the system automatically identifies related images and/or medical image exams from 2, 3, or 4 (or more) other exams and displays the images next to one another in a grid arrangement, and/or sorts the images and displays them sequentially in an image pane.

In an embodiment, a user interface of the system includes one or more image panes in which medical images may be displayed. As described in further detail below, such a user interface may provide one or more comparison panes on a display device in which images from multiple image series are sequentially displayed.

In various embodiments, medical images may be reconstructed and/or rendered from 3D or volumetric image data using methods including multiplanar reformation/reconstruction (MPR), maximum intensity projection (MIP), and/or the like. Such rendered images may be rendered to match comparison images from other image series and/or exams so as to enable more efficient comparison and evaluation by the user.

Rendering and/or reconstruction of images from 3D volumetric image data can be a computationally intensive task that requires significant processing power. Three-dimensional medical image data sets can be on the order of multiple gigabytes in size, therefore requiring efficient computer algorithms to generate human-useable images and other information. Typically, such 3D data sets are acquired by CT, MRI, and/or other similar modality. Rendering (e.g., rendering 2D projections of 3D data sets) may be accomplished in various ways, e.g., direct volume rendering, maximum intensity projection, minimum intensity pixel displays, multiplanar reconstruction, and/or the like, and may require one or more computational optimization techniques to be fast enough to be useful.

While the use of medical imaging data (e.g., medical images) is described in the example embodiments herein, in various embodiments the systems and methods described may be used for display of, and interaction with, non-medical information, for example, seismic information, weather data, and/or financial data, among others.

Additionally, while the examples herein describe the use of information acquired from a physical object such as a patient, the systems and methods described may be used to display information obtained or generated in other ways, for example, information calculated in a simulation (for example, a financial simulation, and/or a physics simulation, among others). The systems and methods described herein may be used for display of any type of information that can be represented on a digital display.

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

II. Definitions

In order to facilitate an understanding of the systems and methods discussed herein, a number of terms are defined below. The terms defined below, as well as other terms used herein, should be construed broadly to include the provided definitions, the ordinary and customary meaning of the terms, and/or any other implied meaning for the respective terms. Thus, the definitions below do not limit the meaning of these terms, but only provide exemplary definitions.

User: Also referred to herein as "reviewer" and/or "viewer." An individual (or group of individuals) that interfaces with a computing device to, for example, view medical images. Users may include, for example, physicians (including, for example, doctors, radiologists, etc.) hospital staff, and/or any other individuals (including persons not medically trained) involved in analysis, annotation, comparison, acquisition, storage, management, or other tasks related to medical images (or any other types of images) as described herein. Any discussion herein of user preferences and/or rules associated with users should be construed to also, or alternatively, include user group preferences (or rules associated with groups of users), site preferences/rules, system preference/rules, and/or default software preferences/rules.

Medical Image (also referred to herein as an "Image"): Any type of image of an organism (e.g., a human patient). It may include but is not limited to a radiograph (e.g., an x-ray image), computed tomography (CT), magnetic resonance imaging (MRI), ultrasound (US), mammogram, positron emission tomography scan (PET), nuclear scan (NM), pathology, endoscopy, ophthalmology, or many other types of medical images. As mentioned above, medical images may be reconstructed and/or rendered from 3D or volumetric image data using methods including multiplanar reformation/reconstruction (MPR), maximum intensity projection (MIP), and/or the like (including, e.g., any Computerized Advanced Processing (CAP), as described below). Images of the present disclosure also include "multi-frame" images, which are images comprising multiple frames (also referred to herein as sub-images). For example, a multi-frame image may be played as a movie (e.g., showing a beating heart, where each frame shows the beating heart at a different point in time). FIG. 3 illustrates an example of a medical image 312 and possible attributes that may be associated with a medical image. While this description is directed to viewing and tracking of medical images, the methods and systems described herein may also be used in conjunction with non-medical images, such as, images of circuit boards, airplane wings, and satellite images, for example.

Modality: A medical imaging method (e.g., a patient who undergoes an MRI is said to have been scanned with the MRI modality).

Image Series (also referred to herein as a "Series"): Any two or more images that are related. Images in a series typically share one or more common attributes, for example, a type of anatomic plane and/or an image orientation. For example, an image series may comprise two or more images of a particular patient that are acquired on a particular date, e.g., different x-ray projections of the chest. A series of contiguous 3 mm axial CT scans of the chest is another example of an image series. A brain MRI scan might include the following series: sagittal T1 weighted images, axial T1 weighted images, axial FLAIR images, axial T2 weighted images, as well as post contrast axial, sagittal and coronal T1 weighted series. An image series of an exam may be identified by its "type" (also referred to herein as a "series type" and/or a "view type"). For example, series may be acquired using different pulse sequences, acquired in different anatomic planes (also referred to herein as "imaging planes"), and/or acquired before or after administration of intravenous contrast material. An image series may be limited to images of a certain modality or may comprise images of multiple modalities. FIG. 3 illustrates an example of an image series 308, as well as example attributes that may be associated with an image series. As shown, the image series 308 includes multiple medical images, such as medical image 312.

Montage: An arrangement of images. In some implementations, a montage may itself be an image which comprises two or more images stitched together into a single image in a particular arrangement. In some implementations, a montage may be a file comprising sufficient information regarding each image of the montage so that the entire montage can be recreated upon display of the montage.

Patient: An individual who undergoes a medical imaging examination.

Clinical Data Elements: Medical data, such as related to patient or population demographics, diagnosis, exposure, family history, or treatment. For example, specific clinical data elements may include ethnicity, gender, race, year of birth, year of death, signs, symptoms, referring doctor concern, age at diagnosis, last known disease status, morphology, primary diagnosis, prior malignancy, progression or recurrence, site of resection or biopsy, tissue or organ of origin, tumor grade, tumor stage, vital status, alcohol history, alcohol intensity, BMI, cigarettes per day, height, smoking history, smoking intensity, weight, years smoked, relationship age at diagnosis, relationship gender, relationship type, relative with cancer history, days to treatment, therapeutic agent, treatment intent type, treatment or therapy, etc.

Medical Imaging Exam (also referred to herein as a "Medical Exam" and/or an "Exam"): A collection of data related to an examination of a patient. May be specific to a particular time or time period. Generally includes one or more medical images and/or image series, montages, reports, notes, graphs, measurements, annotations, videos, sounds or voice data, diagnoses, and/or other related information. May include multiple image series of multiple modalities, volumetric imaging data, reconstructed images and/or rendered images. For example, an exam of a patient may be the brain MRI scan mentioned above, and may include each of the image series obtained on a particular date including: sagittal T1 weighted images, axial T1 weighted images, axial FLAIR images, axial T2 weighted images, as well as post contrast axial, sagittal and coronal T1 weighted series. Another example of an exam may be a dual-energy radiography exam, which may include image data including traditional x-ray image images, bone subtracted (or "bone out") x-ray images, and/or tissue subtracted (or "tissue out") x-ray images. FIG. 3 illustrates two example medical exams 302 and 304. As shown, each medical exam 302 and 304 includes multiple image series, such as image series 308 which is a part of medical exam 304.

Image Characteristic: Any characteristic related to display of an image. Includes without limitation, image angle (e.g., an angle of an image with reference to a standard one or more planes of human anatomy; also referred to herein as "scan plane"), anatomical position (and/or location) (e.g., a location, with reference to a standard one or more planes of human anatomy, of the patient represented in a particular image), image orientation (e.g., an orientation of the image with reference to a standard one or more planes of human anatomy), image rotation (e.g., a rotation of the image with reference to a standard one or more planes of human anatomy), image field of view, slice thickness, image window and/or level (e.g., a contrast of the image, a brightness of the image, and/or the like), image color map (e.g., that includes information for rendering different pixel intensities as different colors), other color characteristics, image opacity (and/or opacity map), image zoom level, image cropping information, and/or the like. In some instances, one or more image characteristics may be user defined and/or based on user preferences. Image characteristics are also referred to herein as image "attributes." Further examples of attributes are described below.

Attribute: Any characteristic associated with a data item (e.g., a data item such as a medical exam, an image series, a medical image, and/or the like). Attributes may be inherited in a hierarchical manner. For example, a medical image may inherit attributes of an image series of which it is a part, and an image series may inherit attributes of a medical exam of which it is a part. Attributes may be stored as part of an associated data item (e.g., as metadata, DICOM header data, etc.) and/or separately from an associated data item. FIG. 3 illustrates various example attributes that may be associated with exams (e.g., example attributes 306), image series (e.g., example attributes 310), and images (e.g., example attributes 314).

Image Pane: Also referred to herein as "image frame," "viewing pane," "viewing frame," "comparison pane," "comparison frame," and/or simply "pane." A region of a computer display that may display an image.

Annotation: Any notes, measurements, links, assessments, graphics, and/or the like, associated with a data item, either automatically (e.g., by one or more CAP, described below) or manually (e.g., by a user). For example, when used in reference to a medical image, annotations include, without limitation, any added information that may be associated with the image, whether incorporated into an image file directly, comprising metadata associated with the image file, and/or stored in a separate location but linked to the image file in some way. Examples of annotations include measurements by using linear dimensions, area, density in Hounsfield units, optical density, standard uptake value (e.g., for positron emission tomography), volume, curved lines (such as the length of a curved vessel), stenosis (e.g., percent narrowing of a vessel at a certain location relative to a reference location), or other parameters. Additional examples of annotations include arrows to indicate specific locations or anatomy, circles, polygons, irregularly shaped areas, notes, and/or the like. Additional examples of annotations include arrows to indicate specific locations or anatomy, circles, polygons, irregularly shaped areas, notes, and/or the like. Further examples of annotations include graphics that, for example, outline lesions, lumbar discs, and/or other anatomical features.

Computerized Advanced Processing (CAP): Any computerized image analysis, image analysis technique, and/or image processing technique discussed herein, and/or any similar computerized processing technique that is currently or later available. CAP is described herein with regard to radiology images, but CAP and the systems and methods described herein may be applied in other areas including, but not limited to, other types of medical images (for example, cardiology, dermatology, pathology and/or endoscopy, among others), computer generated images (for example, 3D images from virtual colonoscopy, 3D images of vessels from CTA, and the like), images from other fields (for example, surveillance imaging, satellite imaging, and the like), as well as non-imaging data including audio, text, and numeric data. In some embodiments, CAP may include, but is not limited to, volume rendering (including, for example, multiplanar reformation/reconstruction (MPR), maximum intensity projection (MIP), 3D volume rendering, and/or 3D surface rendering), graphical processing/reporting (e.g., automated identification and outlining of lesions, lumbar discs etc.), automated measurement of lesions or other anatomical features, other image processing techniques, and/or the like.

User Input (also referred to herein as "Input"): As used herein in reference to user interactions with data displayed by a computing system, "user input" is a broad term that refers to any type of input provided by a user that is intended to be received and/or stored by the system, to cause an update to data that is displayed by the system, and/or to cause an update to the way that data is displayed by the system. Non-limiting examples of such user input include keyboard inputs, mouse inputs, digital pen inputs, voice inputs, finger touch inputs (e.g., via touch sensitive display), gesture inputs (e.g., hand movements, finger movements, arm movements, movements of any other appendage, and/or body movements), and/or the like. Additionally, user inputs to the system may include inputs via tools and/or other objects manipulated by the user. For example, the user may move an object, such as a surgical instrument, tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand and/or a 3D mouse.

Data Store: Any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

Database: Any data structure (and/or combinations of multiple data structures) for storing and/or organizing data, including, but not limited to, relational databases (e.g., Oracle databases, mySQL databases, etc.), non-relational databases (e.g., NoSQL databases, etc.), in-memory databases, spreadsheets, as comma separated values (CSV) files, eXtendible markup language (XML) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

III. Example Computing Devices and Systems

FIG. 1 is a block diagram showing various aspects of a Conversation Management System 150 and network environment 100 in which the Conversation Management System 150 may be implemented, according to various embodiments of the present disclosure. The Conversation Management System 150 may be referred to herein as the "conversation system," the "medical image computing system," simply the "system," and/or the like.

As shown, the network environment 100 may include the computing system 150, a computer network 190, an image store 122, a medical knowledge base 120, a user preferences and rules database 124, one or more optional external sensors 125, one or more imaging devices 170, and/or a clinical decision support (CDS) server 171. As described below, in various embodiments the computing system 150, the image storage 122, the medical knowledge base 120, the user preferences and rules database 124, the external sensor(s) 125, the imaging devices 170, and/or the CDS server 171 may be in communication with one another via the network 190. In some embodiments, various of the image storage 122, the medical knowledge base 120, the user preferences and rules database 124, the external sensor(s) 125, the imaging devices 170, and/or the CDS server 171 may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150. Depending on the embodiment, the system 150 may include one or more separate computing devices (e.g., desktop computer, mobile computer, cell phone, server, etc.) that implement the various functionality discussed herein.

The computing system 150 may include various components as shown and described in detail below. As described below, the computing system 150 may display images (including, e.g., medical images) and/or other data to a user via a display 155. The computing system 150 may include one or more sensors 161 (and/or one or more external sensors 125) that detect input from a user (e.g., gesture inputs via hand motion). Inputs may also be received via the input devices 156 described below. Sensors 161 may take various forms and may utilize, for example, cameras that utilize visible light, cameras that utilize infrared light, ultrasonic sensors, etc. Sensors 161 may be placed in a variety of positions that allow visualization of a body part to be monitored. As described below, in response to user input received by the computing system 150 (including, e.g., detected motion of a user's hand and/or other body part and/or inputs via the input devices 156), information displayed (e.g., medical images) may be updated.

Additional components of the computing system 150 may include, for example, one or more processors 152 and memory and/or data storage 153 (including one or more software modules 151 and/or a rules engine 163 (which may itself comprise a software module)). In particular, as described below, the rules engine 163 may execute various rules (for example, one or more rules stored in the user preferences and rules database 124) that may be used to translate various user inputs into corresponding changes of displayed images and/or other data. In another example, various rules of the user preferences and rules database 124 may indicate user preferences for sorting of images having certain attributes, automatic selection of images for comparison with a user selected image, preferences for registration of sorted and/or comparison images, selection of CDS data, and/or the like.

Additional components of the computing system 150 may include sensors 161, which may include, for example, motion sensors 159, orientation sensors 160, and/or location sensors 162. The various sensors 161 may include, for example, a camera (for example, video cameras, infrared cameras, and/or the like) or array of cameras capable of detecting (and/or providing data necessary for detecting) a position (including a location and/or orientation) and/or motion of the user's hand (or other gesture from the user). For example, sensors 161 may comprise a commercially available position sensor such as Microsoft's Kinect or Leap Motion's Leap Motion Controller. In various embodiments, one or more, or in some cases all, of the sensors 161 may be located as external sensors 125. In some embodiments, combinations of external sensors 125 and sensors 161 of the computing system 150 may be used for detecting user inputs.

In some embodiments, one or more sensors (for example, external sensors 125) may be attached and/or removably attached to the user, and/or may be located in tools or other objects operated by the user (e.g., a surgical instrument, tool, stylus, or wand, as described above) and such sensors may transmit information to the computing system 150 (through either a wired or wireless connection) such that the inputs of the user may be determined. For example, such sensors on the user may include gyroscopes (that may be used, for example, to detect and measure rotational motion), accelerometers (that may be used, for example, to detect and measure linear motion), compasses, Global Positioning System (GPS) transceivers and devices, near field communication (NFC) technology devices, Radio Frequency Identification (RFID) devices, systems and devices utilizing WiFi, systems and devices utilizing Bluetooth such as iBeacons, and/or the like. In another example, a position transmitter may be used to track the location, position, movement, and/or orientation of the user and/or the user's body parts (e.g., the user's hand). Such a position transmitter may transmit a position and/or motion of, e.g., the user's hand and/or an input device, to one of the external sensors 125. In some embodiments position information from the external sensors 125 may supplement position information from the sensors 161. In other embodiments, a user inputs may be determined based on only information from sensors 161 or based on only information from external sensors 125.

The various sensors and transmitters (e.g., any combination of the sensors described above) may provide input data to the computing system 150 such that inputs from the user may be detected and/or determined. Such input data may be processed by, for example, one or more software modules 151 of the computing system 150 and/or other components of the system, as described below, such that displayed image data and/or other displayed information may be updated.

As further described below, network environment 100 may include a medical knowledge base 120 comprising one or more servers and/or other computing systems storing various types of medical information by the artificial intelligence of the conversation management system 150 that is used in conversing with a user viewing medical data, such as PACS imaging data. In some embodiments, the medical knowledge base 120, or portions of the medical knowledge base 120, may be part of the system 150 and/or available via a local network, rather than via a wide area network or the Internet.

Network environment 100 may include image storage 122 (for example, a data store, database, and/or storage system) that may be configured to store information, such as image data (also referred to herein as image and/or imaging information) (for example, images (e.g., two-dimensional (2D) images), image series, three-dimensional (3D) imaging data, medical imaging exams, and/or the like), that is processed by medical knowledge base 120 and/or computing system 150. In various embodiments, image data is stored in Digital Imaging and Communications in Medicine ("DICOM") format and/or any other appropriate format. Network environment 100 may also include user preferences and rules database 124 which may store user, group, or site preferences and rules that determine the operation of various embodiments as described herein. Additionally, user preferences and rules database 124 may include various rules that are used by the system to translate user inputs into corresponding movement of displayed images and/or other data, as described below.

In some embodiments, user preferences and rules database 124 may be used to store particular rules and preferences to apply to conversational computing data (or other data types in other embodiments) for particular users. For example, certain rules may be preferred by certain users and/or groups of users. Accordingly, preferences associated with those certain users and/or groups of users may indicate that the certain rules are to be applied such that, for example, certain related medical data is analyzed to gain context of the user in developing conversational options to automatically provide to the user.

In various embodiments, the functionality provided by image storage 122, medical knowledge base 120, CDS server 171, and/or user preferences and rules database 124 may reside within computing system 150.

The imaging devices 170 may include any devices capable of obtaining images for use by the system. For example, imaging devices 170 may include one or more medical scanners, such as X-Ray scanners, MRI scanners and/or CT scanners (as further described below).

The clinical decision support (CDS) server 171 may provide any type of imaging and/or other data (referred to herein a clinical decision support (CDS) data) to the computing system 150 that may be useful for analysis and evaluation of images by a user (e.g., for more efficient diagnosis of medical conditions). Determination of CDS data may be by execution of one or more rules of the user preferences and rules database 124. For example, the CDS server may, in response to a request by a user for CDS data in relation to a series of medical images, analyze one or more characteristics associated with a patient from which the series was obtained. The CDS server 171 may then determine, based on the analysis, including accessing relevant information in one or more medical knowledge bases, a next audible output to provide to the user, such as to further a conversation with the user.

IV. Example User Interfaces for Comparison of Images

Figure 2:
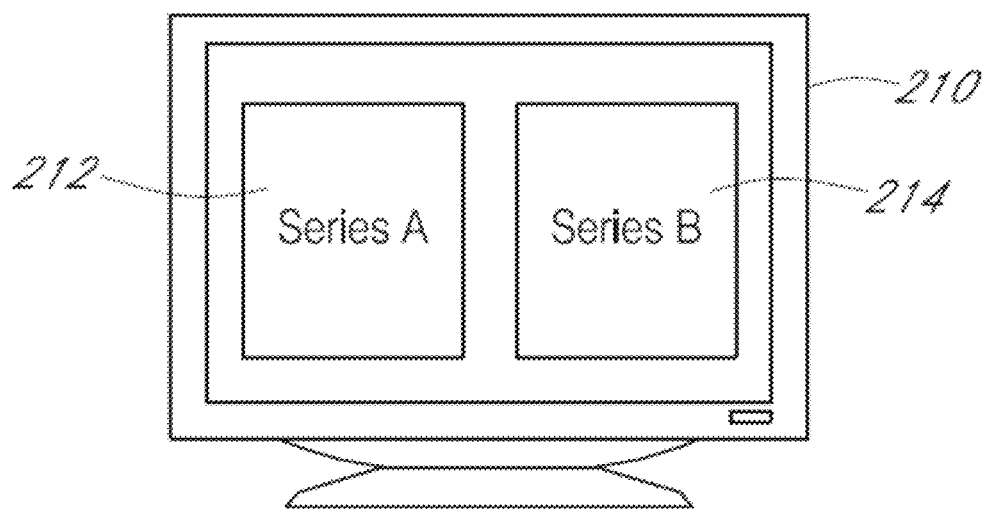
FIG. 2 is a diagram illustrating a display device of the system having images from two image series concurrently displayed in image panes displayed on the display device, according to an embodiment of the present disclosure.

FIG. 2 is a diagram illustrating a display device of the system having images from two image series concurrently displayed in image panes 212 and 214 displayed on the display device 210, according to an embodiment of the present disclosure. In the discussion that follows, the display device 210 is coupled to a computing device, such as computing system 150, and receives display information from the computing system 150. While the systems and methods described below for providing a conversational computing interface may be controlled by any suitable computing device, for ease of explanation herein, reference will be made to a display device coupled to computing system 150.

In one embodiment, a physician views a medical imaging exam. For example, the physician may say, "Show two priors of the same body part," and the system displays two prior imaging exams of the same body region in the same patient, such as in the image panes 212, 214 of FIG. 2. For example, the conversational computing system may determine context of the current users activities (e.g., in viewing medical images on a PACS system), access a medical knowledge base to determine the most likely images of interest to the user, in view of translation of the audio input to determine that the request is for two priors of the same body part (as currently displayed), and automatically select and display prior images. Thus, the images (or image series) displayed in image panes 212, 214 may be automatically selected by the system 150.

In another example, the physician may say, "Show two priors, any body part," in which case the system 150 may show the two most recent prior exams of the same patient independent of body part. The system may be responsive to audio input or manual input in order to determine the system's audio output based on its combined understanding of patient related information, image analytics, and medical knowledge. For example, the physician may say, "there is a posterior fossa enhancing mass" and the system may respond, "Shall I create a tumor tracking table?" In some embodiments, the database 124 stores the criteria, preference, rules, etc. for matching spoken words or phrases from the user with particular actions (also referred to as "intent of action" herein). The database 124 may be updated by the user, user group, administrator, or other, to include additional levels, criteria, and/or preferences for matching user utterances with particular actions. In some embodiments, such updates may be determined automatically by the system 150, such as based on machine learning analysis of prior interactions with similar medical data by the user and/or related user groups.

In some embodiments, the system may recognize reported findings provided by a user (e.g., by voice commands and/or other inputs) and automatically respond to the reported findings by offering clinical correlations (e.g., via audio and/or visual outputs). For example, the physician says, "There is moderate bilateral renal atrophy," and the system responds, "The patient's renal function shows a serum Cr of 2.4 and a GFR of 28.

In some embodiments, the system 150 may continuously maintain a prioritized listing of possible actions, such as based on state of the current conversation with the user, patient medical data, computer-aided diagnostics, etc., and display portions of the prioritized listing in response to user command and/or other triggers (e.g. a possible action may be automatically provided to the user when a risk level to the patient exceeds a predefined threshold). For example, a physician may ask, "what else should I worry about?" to trigger the system to respond with "This enhancing posterior fossa mass could be a hemangioblastoma. If so, this could be Von Hippel Lindau syndrome . . . also look for renal tumors. Would you like to view the prior abdomen CT? Would you like me to add this recommendation to the report?" The audio information may be provided in visual form also, such as in a list of the audio recommendations provided.

In addition to these various embodiments, the system may use conversational human interfaces to help the user set preferences, for example, configuring rules for when the system should interrupt the user with one or more recommended action. For example, one user might want to be interrupted only during dictation pauses (e.g., after a two second pause), another at the conclusion of the report (e.g., after indicating completion of the report or providing information in required portions of the report), and yet another in response to marking a lesion as a possible tumor (e.g., immediately upon providing the "tumor" marker via voice or other input), or yet another, if image analyses (e.g., prior and present) don't reconcile.

Advantageously, the system implements deep learning algorithms to track and learn from the user's behavior with regard to conversational interface itself as well as the services that will be incorporated into each session. For example, based on the user's behavior, the conversational interface may offer advice about training if it detects user behaviors that signify a beginner. In another example, the system may offer differential diagnoses if it notices that the user is not mentioning differential diagnoses, or it may curtail this activity if the user repeatedly answers no to such an offer for help. The system may self-tailor the nature, frequency, and/or timing of the assistance it provides in this manner.

In addition to reading assistance, the conversational interface provided by the conversation management system 150 may also be responsive to workflow commands, such as "show me the exams in order of severity" or "show me any emergency room exams now" or "show me exams marked STAT." The interface might also provide answers to workflow pace questions, for example, by prompting the user to slow down or speed up, or by telling the user about exams that are in queue waiting to be read.

Thus, the system combines multiple technologies in a novel way to provide cognitive assistance to users so that the users may maintain visual attention on the computer display.

Figure 4:
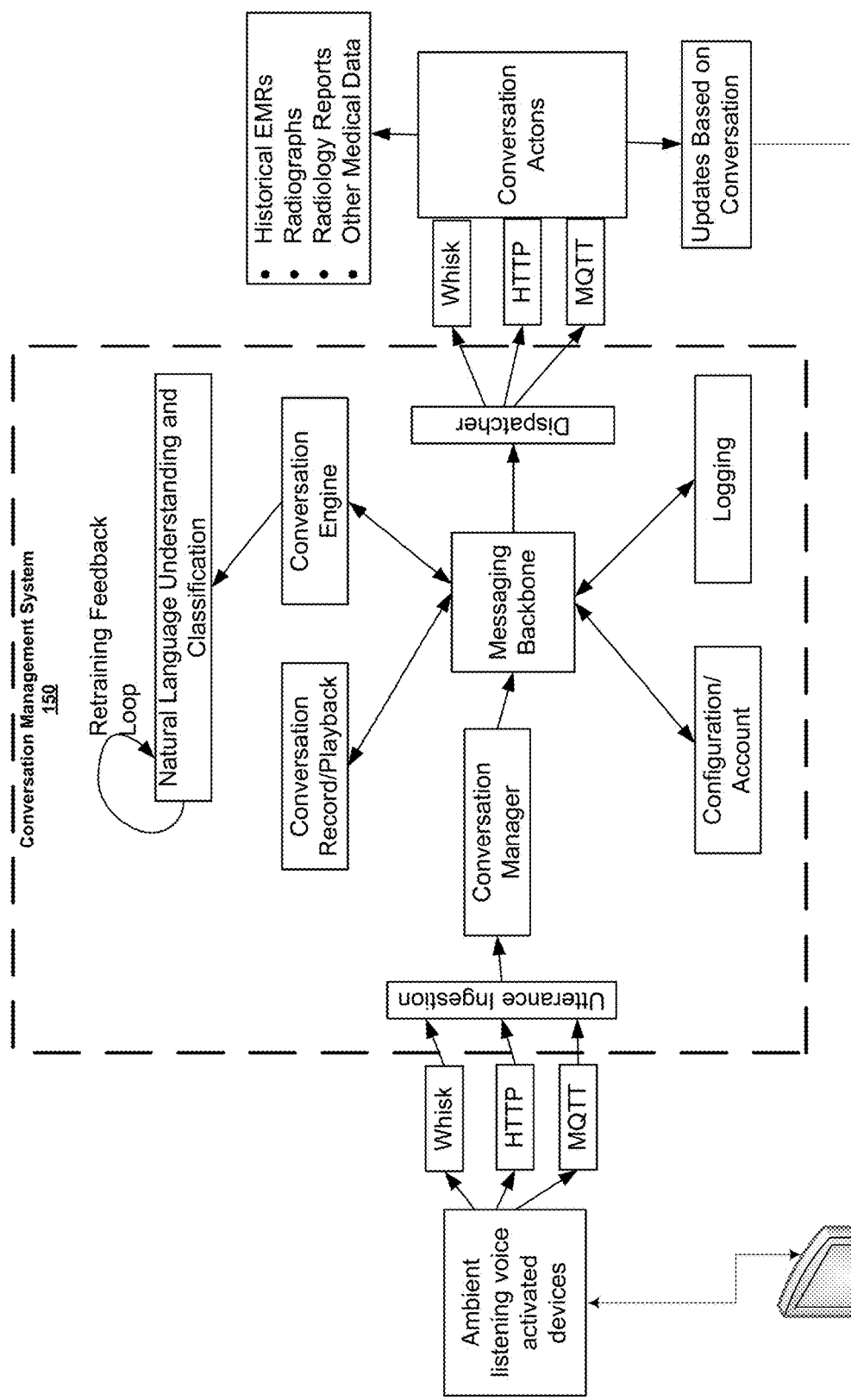
FIG. 4 is a block diagram of an example Conversation Management System, including various components, that may be configured to perform the processes discussed herein, according to embodiments of the present disclosure.

FIG. 4 illustrates an example configuration and architecture of a conversational computing system. Each of the blocks in FIG. 4 may be computing devices or modules executable on a computing device, or the blocks may be combined or further separated into fewer or additional computing devices or modules.

In the example of FIG. 4, a physician initiates interaction with the conversational interface through a voice based utterance captured by an ambient listening device, such as a microphone or other audio sensor. The utterance arrives at the ingestion point through one or more of variety of internet protocols, for example MQTT, HTTP, or OpenWhisk protocols. After receiving the utterance (or a portion of the utterance), the system interprets the utterance to determine what the physician is asking to be performed. For example, the utterance may be placed on the message backbone for processing by a Conversation Engine (CE).

In the example of FIG. 4, the Conversation Engine is responsible for converting a natural language request (e.g. "Show two priors, any body part.") into an "Intent of Action" format, such as based on user-provided and/or artificial intelligence-generated rules, criteria, models, etc. for determining recommended user feedback and/or actions. In this embodiment, an "Intent of Action" is a digital representation or data structure of what the natural language processing model believes has been requested. The "Intent of Action" identified by the Conversation Engine may then be placed onto the message backbone for processing by the Dispatcher.

In some embodiments, the Conversation Engine (CE) may be implemented using the IBM Watson™ Conversation service configured as an application that understand natural-language input and use machine learning to respond to user in a way that simulates a conversation between humans. In some embodiments, the CE is stateless, that is, the services does not maintain the State of a conversation. In this embodiment, the Conversation Manager and/or other invoking component stores the state information. In other embodiments, the CE itself maintains the state of conversations.

In the example of FIG. 4, the dispatcher is configured to locate and activate any Conversation Actions (CA) associated with the determined Intent of Action, e.g., without further user interaction. Conversation Actions are the executable skills that carry out the physician's request. For example, with reference to the utterance "Show two priors, any body part," the determined CA may perform the following:

Establish context of viewing activity, including patient history and previous digital assets (e.g. EMR, Radiology Reports, radiographs, image analysis)

Determine quantity of prior images to display (e.g. show two priors, any body part)

Choose "any body part"

Communicate with Viewing device to deliver the requested information (e.g., the selected prior exams)

Deliver output text (audio, or other audio/visual information) to be provided to the physician affirming the action was carried out as appropriate, providing detailed information regarding the actions performed, providing recommended additional actions that may be performed, and the like Update state of the conversation to be used in determining further CA's (e.g., in response to further actions and/or utterances from the user)

In some embodiments, the Messaging Backbone (MB) is configured to provide a communication channel between other components, such as those shown in FIG. 4. In some embodiments, components register with the MB to enable communications. Components may register as either a producer and/or a consumer of information. For example, producers generate work item units that are placed onto the MB while consumers (or "receivers") receive or perform work items requested by producers. This model enables producers and consumers to scale independently as the system gains or sheds load, that is, each individual component may need to scale-up or scale-down to handle peaks and valleys in usage load.

In some embodiments, the Utterance Ingestion component is configured to receive input data from a wide variety of possible input devices. The Utterance Ingestion component may provide an extensible framework for registering new utterance delivery protocols, such as:

HTTP—The Hypertext Transfer Protocol (HTTP) is an application protocol for distributed, collaborative, and hypermedia information systems. HTTP is the foundation of data communication for the World Wide Web.

MQTT—MQTT is a machine-to-machine (M2M)/"Internet of Things" connectivity protocol that was designed as a lightweight publish/subscribe messaging transport OpenWhisk—OpenWhisk is an open source cloud-first distributed event-based programming service. It provides a programming model to upload event handlers to a cloud service, and register the handlers to respond to various events Depending on the implementation, the utterance ingestion component may be configured to perform various functions including one or more of:

receive the message from the ambient listening device
transform device specific message formatting into a general message format understood the by the system
forward the request to the Conversation Manager for fulfillment
transform the message output format from the Conversation Manager into a device specific format associated with the user device.

In some embodiments, the Conversation Manager (CM) is configured to maintain state information (or simple "state") between interactions of the user (e.g., physician) with the system 150. State information may include any data that is relevant to the conversation, such as what is (and has been) displayed, discussed, pointers to medical data (e.g., EMR data), and the like. The state information may also include metadata describing exactly where in a multi-turn conversation the last utterance or turn of the conversation ended.

In some embodiments, the Dispatcher component is configured to monitor or listen to the MB for "Intent of Action" requests and fulfill those work item requests by invoking Conversational Actions. The Dispatcher may be configured to support an extensible framework for registering Conversation Actions that support different protocols, such as HTTP, MQTT, OpenWhisk, and/or others.

Conversation Actions may support one or more of the above protocol formats. Once a response is received from an invocation of a Conversation Action the result of the action may be placed back onto the MB for further process and ultimate delivery to the initiating ambient listening device.

In some embodiments, a Conversation Action (CA) is a functional unit that carries out the requested "Intent of Action" requested by the physician. In the example above where the user speaks "Show two priors, any body part", the CA accesses or determines the State of the conversation. The State information may include and/or be used to determine context of activity, including patient history, previous digital assets, and/or information other CAs may have deposited into the State. As mentioned above, CAs may be implemented using a variety of internet protocols, such as extensible frameworks for registering and handling new protocols.

In some embodiments, the rules for identifying actions associated with combinations of context, user utterances, current state of the conversation, etc., may include criteria for matching related images and/or image series. For example, matching rules may be established to select medical data based upon any of the following non-limiting criteria: modality (e.g., MRI, CT, X-ray, etc.); exam type (e.g., left knee X-ray, CT Chest, MRI Brain, etc.); archive status (e.g., has the exam been archived, archived and restored, not yet archived); assigned physician (e.g., has the exam been assigned to a particular physician for interpretation); exam age (e.g., how long ago was the exam done); patient age; any item in a DICOM header file (e.g., such as orientation, contrast use, thickness of slices, field of view, MRI tissue contrast weighting); time/day of acquisition; and/or any other attribute and/or image characteristic. In further examples, criteria may include information extracted through analysis of images (e.g., via one or more CAP), such as a view type of an image determined through automatic analysis of the image. With regard to some criteria, such as MRI tissue contrast weighting, the rules may analyze the MRI pulse sequence and the imaging parameters in order to determine the tissue contrast weighting and subcategorize images into weighting categories or weighting names.

The matching rules can be used to match medical images in the same and/or different medical series. For example, assume the medical images relate to three series each having 6 x-rays. The matching rules can be established such that like views among each of the different series are grouped together for subsequent viewing. The matching rules be defined using simple or complex search expressions such as "AND" or "OR."

In various embodiments, the user preferences and rules database 124 may include "display rules" that may indicate ways images and/or image series are to be displayed in user interfaces of the system. For example, an image or exam matching particular criteria in the display rules may be displayed with a certain pixel window level or width (similar to brightness and contrast), in color, based on a certain color map, opacity map, or other image characteristics. Display rules may be user-defined allowing the user to determine the timing, positioning, and size of displayed selected/comparison images. For example, a user can define that selected/comparison medical images are all displayed concurrently on a display. Also, for example, a user can define that the most recent of the selected/comparison medical images are displayed on the left hand portion of the display and the other selected/comparison medical images are displayed in sequence on the right hand side of the display, the sequence advancing in response to user prompting. In one embodiment, the display rules include directives (e.g., timing, positioning, and size). As an example, directives can include the following for identifying location information:

TOP_DISPLAY, BOTTOM_DISPLAY, RIGHT_DISPLAY, LEFT_DISPLAY, CENTER_DISPLAY. Furthermore, if the number of comparison medical images is variable, the display rules can include instructions for identifying selected medical images based upon further rules, such as using the matching rules listed above. In addition, the display rules may or may not define how many images or image series are displayed per monitor, a display grid (e.g., 2×3, 5×4, etc.), or whether like images are displayed neighboring each other side by side horizontally or vertically. Furthermore, the display rules may also specify how different selected/comparison medical images from different series may be sorted together for successive display. Using the display rules, the user can provide display rules such that related medical images are readily comparable.

It is noted that the display rules may define user display preferences that are specific for particular types of medical images, e.g., the imaging modality, the body part, whether there is one exam, two, or more medical images being displayed. In one embodiment, one set of display rules can apply to one modality and another set of display rules can apply to another modality. In addition, the display rules may include specific triggers or warnings that occur if the user-defined display rules are not satisfied.

In various embodiments, display rules may be based on any image characteristic, as described above. Further, in some embodiments, display rules may be stored as image characteristics.

In an embodiment, a first user input (e.g., pressing an arrow or pageup/pagedown key, a side-to-side hand gesture movement, etc.) may change displayed image series, while another user input (e.g., a scroll of a mouse wheel, a forward-and-back hand gesture movement, an hand rotation gesture, etc.) may change displayed images. In an embodiment, user inputs may apply to a one of the panes that is currently selected by, e.g., a mouse cursor hovering over the pane, the user's hand being located near the pane, the pane being highlighted in the user interface, and/or the like. In an embodiment, the user interface may enable a user to "lock" certain panes such that the user's inputs only affect "unlocked" panes. Thus, the user may compare other images/image series to a "frozen" image in one or more of the panes. In another example, the user may similarly select a single pane to be "unlocked," causing all the other panes to be "locked."

Figure 5:
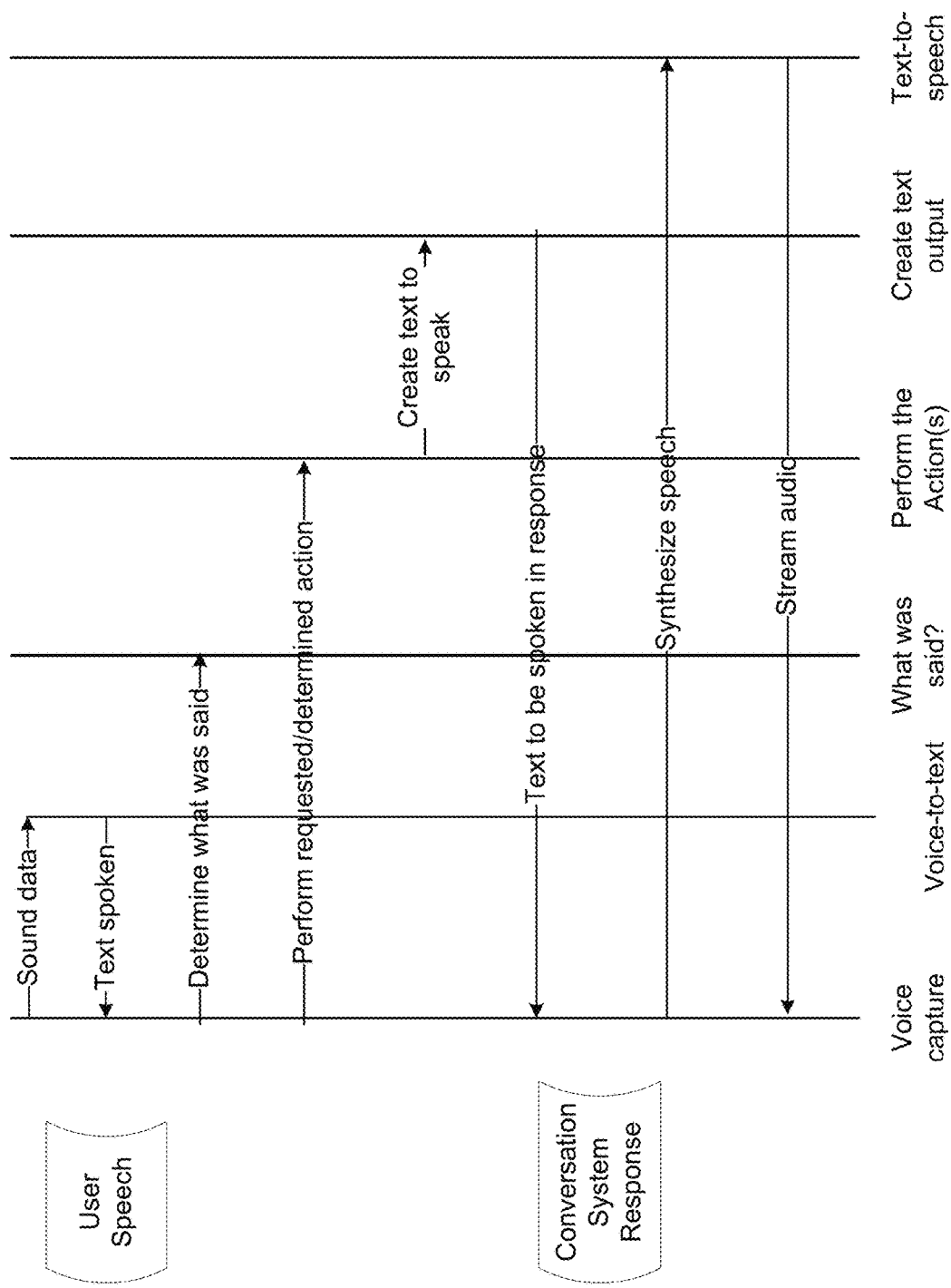
FIG. 5 is a diagram illustrating an example of operations performed by the Conversation Management System, such as in response to a spoken command from the user, according to an embodiment of the present disclosure.

FIG. 5 is a dataflow diagram illustrating examples of data and processes that may be performed by the user computing device and/or conversation management system 150. In general, data/actions associated with arrows pointing left to right are initiated by the user device (e.g., a doctor viewing medical images at a PACS workstation), while data/actions associated with arrows pointing right to left are initiated by the conversation management system 150, such as by one or more of the components or modules discussed herein.

V. Example Computing Systems

Referring again to FIG. 1, various configurations of the computing system 150 and network environment 100 may be used to implement and/or accomplish the systems and methods disclosed herein. For example, the computing system 150 may be configured to display and/or enable a user to view and/or interact with various types of data including two-dimensional images, three-dimensional volumes, and/or or other types of information, as described above.

As described above, the computing system may take various forms. In one embodiment, the computing system 150 may be an information display computing device and/or system, a server, a computer workstation, a desktop computer, a Picture Archiving and Communication System (PACS) workstation, a laptop computer, a mobile computer, a smartphone, a tablet computer, a wearable computer (for example, a head-mounted computer and/or a computer in communication with a head-mounted display), a smartwatch, a mobile computer, a cell phone, a personal digital assistant, a gaming system, a kiosk, an audio player, and/or any other device that utilizes a graphical user interface, such as office equipment, automobiles, airplane cockpits, household appliances, automated teller machines, self-service checkouts at stores, information and other kiosks, ticketing kiosks, vending machines, industrial equipment, and/or a television, for example. In an embodiment the computing system 150 comprises one or more computing devices in communication with one another.

The computing system 150 may include various components including, for example, one or more processors 152, memory and/or data storage 153 (including one or more software modules 151 and/or a rules engine 163 (which may itself comprise a software module)), an operating system 154, a display 155, one or more input devices 156, one or more interfaces 157, an audio input/output 158, and/or one or more sensors 161 (including, for example, zero or more motion sensors 159, zero or more orientation sensors 160, and/or zero or more location sensors 162). Each of the components of the computing system 150 may be connected and/or in communication with each other using, for example, a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing system 150 (as described above and below) may be combined into fewer components and modules or further separated into additional components and modules.

In various embodiments the software modules 151 may provide functionality as described above with reference to the various figures. For example, modules 151 of the computing system 150 may include user input modules, image display modules, motion detection/determination modules, orientation detection/determination modules, position detection/determination modules, location detection/determination modules, patient information display modules, rules engine modules (for example, rules engine 163), user interface modules, and/or the like. For example, each of the motion, orientation, position, and/or location detection/determination modules may determine user inputs and/or gestures such that the user may interact with medical images, as described above. Further, the image display modules and/or the user interface modules may display user interfaces, images, and/or other data on the display 155 in response to user inputs (as described in reference to various embodiments of the present disclosure). Further, the image display modules and/or the user interface modules may be configured and/or designed to generate user interface data useable for rendering the interactive user interfaces described herein, such as a web application and/or a dynamic web page displayed by a computing device. With reference to FIG. 4, the modules 151 of the computing system may include an utterance ingestion, conversation manager, conversation recording/playback, messaging backbone, dispatcher, configuration/account, logging, conversation actions, and/or other related functional modules. In various embodiments the user interface data may be used by the computing system 150, and/or communicated to any other computing device, such that the example user interfaces are displayed to a user. For example, the user interface data may be executed by a browser (and/or other software program) accessing a web service and configured to render the user interfaces based on the user interface data.

As described below, the software modules 151 may include various software instructions, code, logic instructions, and/or the like that may be executed by the one or more processors 152 to accomplish the functionality described above. In other embodiments, software modules 151 may reside on another computing device and/or system, such as a web server or other server (for example, medical knowledge base 120) or other server, and a user may directly interact with a second computing device and/or system that is connected to the other computing device and/or system via a computer network.

The computing system 150 may run an off-the-shelf operating system 154 such as a Windows, Linux, MacOS, Android, or iOS, or mobile versions of such operating systems. The computing system 150 may also run a more specialized operating system which may be designed for the specific tasks performed by the computing system 150, or any other available operating system.

The computing system 150 may include one or more computer processors 152, for example, hardware computer processors. The computer processors 152 may include central processing units (CPUs), and may further include dedicated processors such as graphics processor chips, or other specialized processors. The processors may be used to execute computer instructions based on the software modules 151 to cause the computing system 150 to perform operations as specified by the modules 151. The software modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Objective-C, Swift, JavaScript, ActionScript, Visual Basic, HTML, Lua, C, C++, or C#. While "modules" are generally discussed herein with reference to software, any modules may alternatively be represented in hardware or firmware. In various embodiments, the modules described herein refer to logical modules that may be combined with other modules or divided into sub-modules despite their physical organization or storage.

The computing system 150 may also include memory 153. The memory 153 may include volatile data storage such as RAM or SDRAM. The memory may also include more permanent forms of storage such as a hard disk drive, a flash disk, flash memory, a solid state drive, or some other type of non-volatile storage, as described below.

The computing system 150 may also include or be interfaced to one or more display devices that provide information to the users. Display devices 155 may include a video display, such as one or more high-resolution computer monitors, or a display device integrated into or attached to a laptop computer, handheld computer, smartphone, smartwatch, wearable computer, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers. As described above, images and other information may be displayed to the user via the display devices 155 such that the user may efficiently view and interact with such images and information.

The computing system 150 may also include or be interfaced to one or more input devices 156 which receive input from users, such as a keyboard, trackball, mouse, 3D mouse, dial and/or knob (for example, a smartwatch crown), drawing tablet, joystick, game controller, touch sensitive surface (for example, capacitive or resistive touch screen), touchpad, accelerometer, video camera and/or microphone.

The computing system 150 may also include one or more interfaces 157 which allow information exchange between the computing system 150 and other computers and input/output devices using systems such as Ethernet, Wi-Fi, Bluetooth, as well as other wired and wireless data communications techniques.

The computing system 150 may include the audio input/output 158 for receiving, for example, audio commands or other input from the user. The audio system may also provide audio output to provide audio information to a user, for example via a speaker or headset. As described above, various sensors of the computing system 150 may include, for example, gyroscopes, accelerometers, cameras, Global Positioning System (GPS) transceivers and devices, near field communication (NFC) technology devices, Radio Frequency Identification (RFID) device, systems and devices utilizing WiFi, systems and devices utilizing Bluetooth such as iBeacons, and/or the like. The various sensors may provide input/data to the computing system 150 related to the location, position, orientation, and/or motion of a user, a user's appendage (such as an arm and/or hand), and/or another input device operated by the user. Such information may be processed by, for example, one or more software modules 151 (such as the rules engine 163) as described above, such that displayed image data (or other types of data) may be updated. Additionally, as described above, the system may also include, in some embodiments, external sensors 125 that may also provide data related to user inputs. External sensors 125 may include any of the sensors described herein, and may provide functionality similar to that described herein with reference to the various sensors. In various embodiments, the functionality provided by image storage 122, medical knowledge base 120, and/or CDS server 171, may reside within computing system 150.

The computing system 150 may communicate and/or interface with other systems and/or devices. In one or more embodiments, the computing system 150 may be connected to the computer network 190. The computer network 190 may take various forms. For example, the computer network 190 may be a wired network or a wireless network, or it may be some combination of both. The computer network 190 may be a single computer network, or it may be a combination or collection of different networks and network protocols. Additionally, the computer network 190 may include one or more local area networks (LAN), wide area networks (WAN), personal area networks (PAN), cellular or data networks, and/or the Internet.

Various devices and subsystems may be connected to the network 190. As shown in FIG. 1, for example, the computing system 150 may be in communication with the image storage 122, the medical knowledge base 120, the external sensor(s) 125, the imaging devices 170, and/or the CDS server 171. Image storage 122 may be a database, data store, and/or other electronic or computer-readable medium storage device configured to store, for example, medical images and/or three-dimensional imaging data. Such medical images and/or three-dimensional imaging data may be processed, for example, by the medical knowledge base 120 and/or the computing system 150. Further, the various components of the network environment 100 may be in communication with various other devices that may, for example, capture and provide images and/or other data to the computing system 150. For example, imaging devices 170 may include one or more medical scanners may be connected, such as MRI scanners. The MRI scanner may be used to acquire MRI images from patients, and may share the acquired images with other devices on the network 190. The imaging devices 170 may also include one or more CT scanners and/or X-Ray scanners. The CT scanners and/or X-Ray scanners may also be used to acquire images and, like the MRI scanner, may then store those images and/or share those images with other devices via the network 190. Any other scanner or device capable of inputting or generating information that may be presented to the user as images, graphics, text or sound may be connected to the network 190, including, for example, computing systems used in the fields of ultrasound, angiography, nuclear medicine, radiography, endoscopy, pathology, dermatology, and the like.

Also connected to the network 190 may be a Picture Archiving and Communications System (PACS) and/or PACS workstation. The PACS System may be used for the storage, retrieval, distribution and presentation of images (such as those created and/or generated by the MRI scanner and/or CT Scanner). The medical images may be stored in an independent format, an open source format, or some other proprietary format. A common format for image storage in the PACS system is the Digital Imaging and Communications in Medicine (DICOM) format. In various embodiments, the stored images may be transmitted digitally via the PACS system, often reducing or eliminating the need for manually creating, filing, or transporting film jackets.

The network 190 may also be connected to a Radiology Information System (RIS). In an embodiment, the radiology information system may be a computerized system that is used by radiology departments to store, manipulate and distribute patient radiological information.

Also attached to the network 190 may be an Electronic Medical Record (EMR) system. The EMR system may be configured to store and make accessible to a plurality of medical practitioners computerized medical records. Also attached to the network 190 may be a Laboratory Information System. In an embodiment, the Laboratory Information System may be a software system which stores information created or generated by clinical laboratories. Also attached to the network 190 may be a Digital Pathology System that may be used to digitally manage and store information related to medical pathology.

Also attached to the network 190 may be one or more Computer Aided Diagnosis Systems (CAD) systems that are generally used to perform Computer-Aided Processing (CAP) such as, for example, CAD processes. In one embodiment, the CAD systems functionality may reside in a computing device and/or system separate from computing system 150 while in another embodiment the CAD systems functionality may reside within computing system 150.

Also attached to the network 190 may be one or more Processing Systems that may be used to perform computerized advanced processing such as, for example, computations on imaging information to create new views of the information, for example, volume rendering and/or other types of processing, for example image enhancement, volume quantification, blood-flow quantification, and the like. In one embodiment, such processing functionality may reside in a computing device and/or system separate from computing system 150 while in another embodiment the processing functionality may reside within computing system 150.

In other embodiments, other computing devices and/or systems that store, provide, acquire, and/or otherwise manipulate medical data may also be coupled to the network 190 and may be in communication with one or more of the devices illustrated in FIG. 1, such as with the computing system 150.

Depending on the embodiment, other devices discussed herein may include some or all of the same components discussed above with reference to the computing system 150 and may perform some or all of the functionality discussed herein.

As mentioned above, various of the image storage 122, the medical knowledge base 120, the user preferences and rules database 124, the external sensor(s) 125, the imaging devices 170, the CDS server 171, and/or other components described above may or may not be considered a part of the computing system 150. For example, in some embodiments one or more of these components may be implemented as part of the computing system 150, may be in direct communication with the computing system 150, and/or may be in indirect communication (e.g., over network 190) with the computing system 150.

VI. Additional Embodiments

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure.

It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A computing system configured to conduct conversations with a user regarding review and analysis of medical data, the computing system comprising:
   a computer processor configured to execute software instructions;
   an audio input device configured to provide an audio input to the computer processor; and
   one or more tangible non-transitory computer readable medium storing:

a medical knowledge database storing medical information regarding a plurality of clinical data elements, including correlations between respective medical symptoms and medical diagnoses;

a messaging backbone configured to receive messages from message producers and provide messages to message consumers; and a plurality of compute engines including at least software code configured for execution by the computer processor, the compute engines including at least:

an utterance ingestion engine configured to convert portions of the audio input to corresponding textual input;

a conversation manager configured to dynamically update a state of a conversation between the user and the computing system;

a conversation engine configured to determine an intent of action of the user; and a dispatcher configured to determine a first action based on the textual input, the intent of action, context of viewing activity by the user including medical images and data previously provided to the user as a result of a conversation action, information in the medical knowledge database, and the state of the conversation, wherein the textual input includes a request for prior images of a patient represented within a currently-displayed image, wherein the first action includes providing first speech output to the user, automatically accessing the medical knowledge base to determine images of interest to the user, automatically selecting, from image storage, a plurality of prior images of the patient, and displaying the plurality of prior images of the patient for comparison by the user, wherein the computer processor is further configured to maintain a prioritized list of possible conversation actions, display portions of the prioritized listing in response to user input, and display at least a portion of the prioritized listing in response to a risk level to the patient exceeding a predetermined threshold, and wherein the dispatcher is further configured to, in response to second input from the user including a workflow command determine a second action based on the second input, the second action including providing second speech output to the user prompting the user to slow down, and provide the second speech output to the user.

2. The computing system of claim 1, further comprising:
a machine learning engine configured to analyze the determined intent of action of the user, the audio feedback provided to the user, and actions performed by the user subsequent to receiving the first speech output; and determine, based on the analysis, updates to an intent of action determination model used by the conversation engine in determining intent of action of the user.

3. The computing system of claim 1, wherein the audio feedback includes a medical suggestion relevant to the viewing context.

4. The computing system of claim 1, wherein the computing system is a PACS.

5. The computing system of claim 1, wherein the first action indicates a possible syndrome.

6. The computing system of claim 1, wherein the request for prior images includes a predetermined number of images and wherein the plurality of prior images includes the predetermined number of images.

7. The computing system of claim 1, wherein the context of viewing activity by the user includes medical images and data currently displayed and medical images and data previously displayed to the user as a result of the conversation action.

8. The computing system of claim 1, wherein the conversation action include automatically analyzing and sorting the plurality of prior images according to attributes of the plurality of prior images and rules.

9. The computing system of claim 1, wherein the conversation action include automatically registering the plurality of prior images.

10. The computing system of claim 1, wherein second textual input includes an identification of a mass and wherein the dispatcher is configured to determine and initiate second conversation actions based on the second textual input, the second conversation actions including providing second speech output to the user asking the user whether a tumor tracking table should be created.

11. The computing system of claim 1, wherein second textual input includes a reported finding and wherein the dispatcher is configured to determine and initiate second conversation actions based on the second textual input, the second conversation actions including providing second speech output to the user including a clinical correlation for the reported finding.

12. The computing system of claim 1, wherein the dispatcher is configured to determine and initiate second conversation actions based on detected behavior of the user signifying that the user is a beginner, the second conversation actions including providing second speech output to the user including advice about training.

13. The computing system of claim 1, wherein second textual input includes a second workflow command and wherein the dispatcher is configured to determine and initiate second conversation actions based on the second workflow command, the second conversation actions including providing second speech output to the user informing the user about one or more exams in a queue waiting to be read.

14. A computing system comprising:
a picture archiving and communication system (PACS) configured to view medical images;
a medical knowledge database providing information regarding a patient, an exam, and general medical information;
an utterance ingestion engine configured to convert portions of audio input to corresponding textual input;
a conversation manager configured to dynamically update a state of a conversation between the user and the computing system;
a conversation engine configured to determine an intent of action of the user; and
a dispatcher configured to determine a first action based on the textual input, the intent of action, context of viewing activity by the user including medical images and data previously provided to the user as a result of an image management action, information in the medical knowledge database, and the state of the conversation, and initiate the first action at a time determined by user mouse and speech actions, past user behavior and the medical knowledge,
wherein the textual input includes a request for prior images of a patient represented within a currently-displayed image, wherein the first action include providing first speech output to the user, automatically accessing the medical knowledge base to determine images of interest to the user, automatically selecting, from image storage, a plurality of prior images of the patient, and automatically displaying the plurality of prior images of the patient for comparison by the user, wherein the dispatcher is further configured to, in response to second input from the user including a workflow command, determine a second action based on the second input, the second action including providing second speech output to the user prompting the user to slow down, and provide the second speech output to the user.

15. The computing system of claim 14, wherein the time is determined based on understanding of a semantic interpretation of the language spoken by the user of the PACS.

16. The computing system of claim 14, further comprising a deep learning component configured to analyze user behavior and update logic used by the dispatcher correspondingly.

17. A computing system configured to conduct conversations with a user regarding review and analysis of medical data, the computing system comprising:
- a computer processor configured to execute software instructions; and
- one or more tangible non-transitory computer readable medium storing the software instructions, the software instructions including:
  - a messaging backbone configured to receive messages from message producers and provide messages to message consumers; and
  - a plurality of compute engines, the compute engines including at least:
    - an utterance ingestion engine configured to convert portions of audio input to corresponding textual input;
    - a conversation manager configured to dynamically update a state of a conversation between the user and the computing system;
    - a conversation engine configured to determine an intent of action of the user; and
    - a dispatcher configured to automatically select and display two or more medical images of a patient represented in a currently-displayed image for comparison by the user based on the textual input, the intent of action, context of viewing activity by the user including medical images and data previously provided to the user as a result of a conversation action, information in a medical knowledge database storing correlations between respective medical symptoms and medical diagnoses, and the state of the conversation,
  - wherein the dispatcher is configured to display the two or more medical images based on criteria for matching at least one selected from a group consisting of related images and related image studies, the criteria based on archive status, and
  - wherein the dispatcher is further configured to, in response to input received from the user including a workflow command, determine an action based on the input, the action including providing speech output to the user prompting the user to slow down, and provide the speech output to the user.

* * * * *